(12) United States Patent
Arkles et al.

(10) Patent No.: US 8,921,579 B2
(45) Date of Patent: Dec. 30, 2014

(54) PENDANT DIPODAL SILANES HAVING A DISILAPROPYL TERMINUS

(71) Applicant: Gelest Technologies, Inc., Morrisville, PA (US)

(72) Inventors: Barry C. Arkles, Pipersville, PA (US); Youlin Pan, Langhorne, PA (US); Gerald L. Larson, Newtown, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 0 days.

(21) Appl. No.: 14/200,147

(22) Filed: Mar. 7, 2014

(65) Prior Publication Data

US 2014/0275574 A1  Sep. 18, 2014

Related U.S. Application Data

(60) Provisional application No. 61/781,299, filed on Mar. 14, 2013.

(51) Int. Cl.

| | | |
|---|---|---|
| *C07D 303/02* | (2006.01) | |
| *C07F 7/04* | (2006.01) | |
| *C07F 7/12* | (2006.01) | |
| *C07F 7/08* | (2006.01) | |

(52) U.S. Cl.
CPC ............... *C07F 7/12* (2013.01); *C07F 7/0812* (2013.01); *C07F 7/0818* (2013.01)
USPC .......................................... 549/215; 556/482

(58) Field of Classification Search
USPC .......................................... 549/215; 556/482
See application file for complete search history.

(56) References Cited

U.S. PATENT DOCUMENTS

| 7,235,683 B2 | 6/2007 | Janeiro et al. |
|---|---|---|
| 7,265,236 B2 | 9/2007 | Arkles et al. |

OTHER PUBLICATIONS

Nametkin et al., Addition of hydrogen-containing halogen derivatives of disilanomethane to unsaturated hydrocarbons, 1953, Doklady Akademii Nauk SSSR, 93, 285-8.*
Arkles: "Tailoring surfaces with silanes", Chemtech, 7, pp. 766-778 (1977).
Plueddemann: "Silane Coupling Agents"; Plenum Press New York; pp. 1-5; (Aug. 1, 1982).

* cited by examiner

*Primary Examiner* — Kristin Vajda
(74) *Attorney, Agent, or Firm* — Panitch Schwarze Belisario & Nadel LLP

(57) ABSTRACT

Pendant dipodal silanes having formula (I) and methods for their synthesis are provided. In formula (I), R is an organic radical other than methyl and X may be a halogen, an alkoxy group, an acetoxy group, or a dialkylamino group. Films, adhesives, and composites formed from the inventive dipodal silanes generally demonstrate significantly greater hydrolytic resistance and film-forming ability than conventional silanes.

$$RSiX_2CH_2SiX_3 \qquad (I)$$

15 Claims, 1 Drawing Sheet

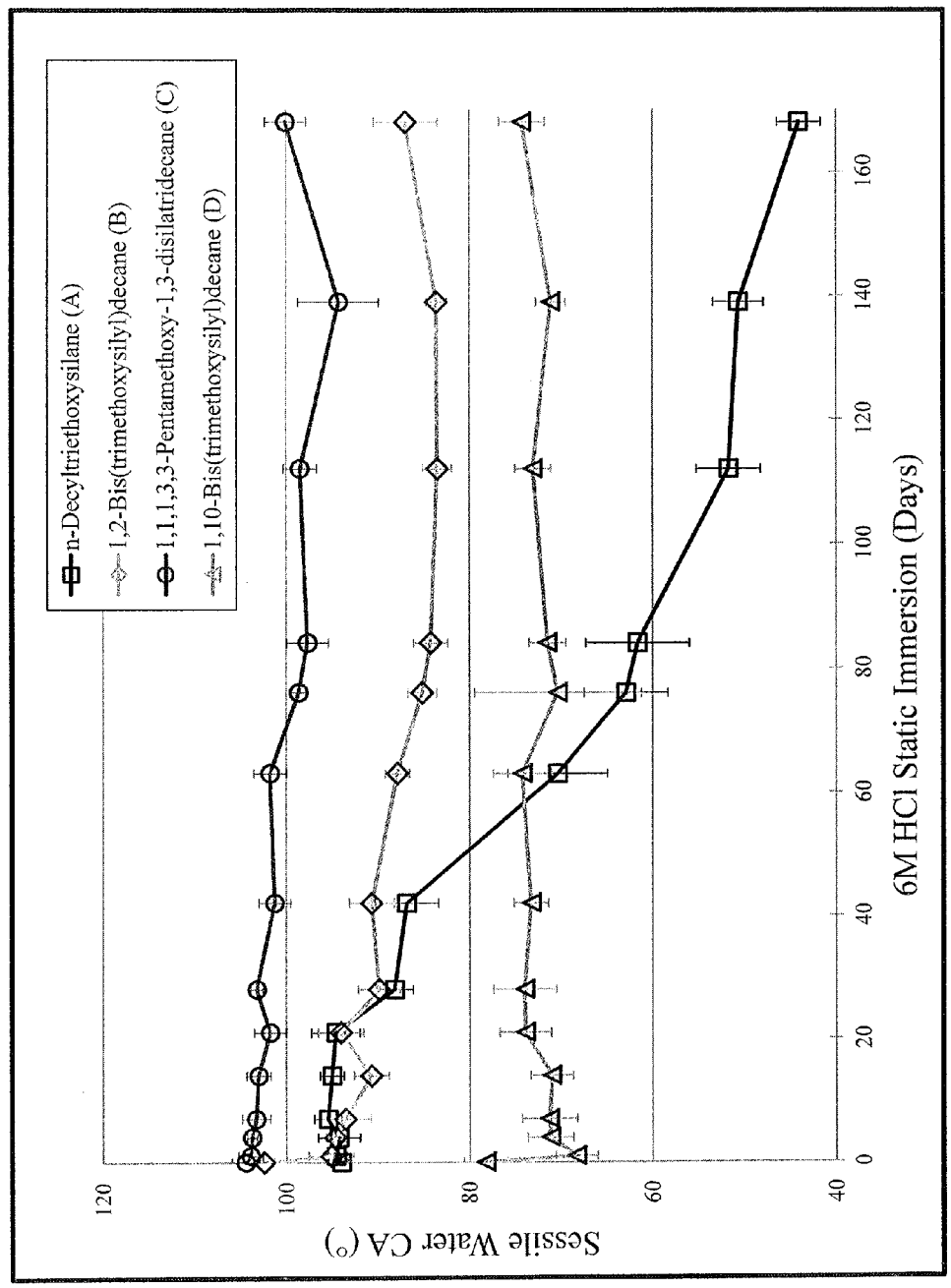

PENDANT DIPODAL SILANES HAVING A DISILAPROPYL TERMINUS

CROSS-REFERENCE TO RELATED APPLICATIONS

This application claims priority to U.S. Provisional Application No. 61/781,299, filed Mar. 14, 2013, the disclosure of which is hereby incorporated by reference.

BACKGROUND OF THE INVENTION

The organosilanes most often utilized in surface modification are silicon chemicals which possess a single hydrolytically sensitive center that can react with inorganic substrates, such as glass, to form stable covalent oxane bonds. These organosilanes also possess an organic substitution which functions to alter the physical interaction of the modified surface with various substrates. The most widely used silanes modify inorganic substrates, such as fiberglass, in order to create a bond with an organic material, such as a polymer, to form reinforced composites. These silanes are often referred to as coupling agents (see, for example, B. Arkles, "Tailoring Surfaces with Silanes," CHEMTECH 7, 766-778 (1977); E. Plueddemann, "Silane Coupling Agents," Plenum, $2^{nd}$ edition (1990)).

Dipodal silanes are silanes that are employed in surface modification and possess two silicon atoms, both of which are capable of bonding to inorganic surfaces through oxane bonds. The term dipodal derives from the Greek suggesting "two feet on the ground," corresponding to the ability of this class of compounds to react with inorganic substrates at two different centers. A salient characteristic differentiating dipodal silanes from conventional silanes is their ability to form bonds that simultaneously exhibit greater hydrolytic stability and greater mechanical strength than the corresponding conventional monopodal silanes.

For the most part, dipodal silanes utilized both commercially and reported in the literature may be regarded as "bridged," that is, each silane substitution is at the terminal end of an organic substitution. Examples of non-functional bridged dipodal silanes include 1,2-bis(trimethoxysilyl)ethane and 1,8-bis(triethoxysilyl)octane. Examples of functional bridged dipodal silanes include bis(trimethoxysilylpropyl)amine and bis(triethoxysilylpropyl)tetrasulfide. However, it has been observed that resistance to hydrolysis and the ability to interact with resins does not appear to be optimized when there are a large number of atoms between the silicon centers and when the functionality is part of the bridging group. An explanation for this behavior may be that a relatively dense siloxane network forms when the hydrolyzable groups are in close proximity to each other, and the ability of the functional group to extend away from the treated surface may be encumbered when it is part of a bridging group.

Relatively few examples of pendant dipodal silanes have been reported. One example is described in U.S. Pat. No. 7,235,683, in which double hydrosilylation of a terminal double bond creates a dipodal silane having the silicon atoms are separated by two carbon atoms. U.S. Pat. No. 7,265,236 provides other examples of dipodal silanes that may be regarded as pendant, but in these cases the two silicon atoms are significantly separated from each other. Accordingly, dipodal silanes in which the silicon centers are in close proximity to each other would be desirable, particularly for use in surface modification.

BRIEF SUMMARY OF THE INVENTION

A pendant dipodal silane according to an embodiment of the invention has formula (I), wherein R is an a linear or branched, saturated or unsaturated, substituted or unsubstituted hydrocarbon having about four to about thirty carbon atoms and X is selected from the group consisting of a halogen, an alkoxy group, a dialkylamino group, and an acetoxy group:

$$RSiX_2CH_2SiX_3 \qquad (I).$$

BRIEF DESCRIPTION OF THE SEVERAL VIEWS OF THE DRAWINGS

The foregoing summary, as well as the following detailed description of the invention, will be better understood when read in conjunction with the appended drawing. For the purpose of illustrating the invention, there are shown in the drawing embodiments which are presently preferred. It should be understood, however, that the invention is not limited to the precise arrangements and instrumentalities shown.

In the drawing:

FIG. 1 is a graph of sessile water contact angle in 6 M HCl versus static immersion time for an inventive material and several comparative materials.

DETAILED DESCRIPTION OF THE INVENTION

This invention is directed to a series of pendant dipodal silanes having a 1,3-disilapropyl terminus. These silanes have formula (I) below, in which R is an organic radical other than methyl and X is a hydrolyzable functionality such as a halogen, an alkoxy group, an acetoxy group, or a dialkylamino group. More preferably, R is a linear or branched, saturated or unsaturated, substituted or unsubstituted hydrocarbon having about four to about thirty carbon atoms. Exemplary halogen groups include chlorine, fluorine, and bromine with chlorine being preferred; exemplary alkoxy groups have one to about ten carbon atoms; preferred alkoxy groups have one or two carbon atoms. The most preferred X groups are chloro, methoxy, and ethoxy groups.

$$RSiX_2CH_2SiX_3 \qquad (I)$$

Appropriate organic radicals include linear, branched, substituted, unsubstituted, saturated, and unsaturated hydrocarbons having four to about thirty carbon atoms, more preferably about four to about thirty carbon atoms including, for example, ethyl, propyl, butyl, isobutyl, hexyl, octyl, isooctyl, decyl, octadecyl, vinyl, allyl, and undecenyl. The hydrocarbons may be substituted with a variety of different types of substituents. For example, hydrocarbons substituted with aromatic groups, such as phenylethyl, phenylpropyl, phenylbutyl, phenylhexyl, and p-methylphenylethyl, are appropriate. The hydrocarbons may also be substituted with ethers, such as methoxyethoxypropyl and methoxypolyethyleneoxypropyl, or with epoxy groups, such as epoxycyclohexyl and glycidoxypropyl. It is also within the scope of the invention for the organic radical to be a saturated or unsaturated ester-substituted hydrocarbon, such as acetoxyethyl, acrylamidopropyl, or methacryloxypropyl. Preferred hydrocarbons are alkyl groups having about two to about thirty carbon atoms, more preferably about four to about thirty carbon atoms, including those with aromatic termini, halogen termini (such as fluoro, chloro, bromo, and iodo), and alkyl groups in which all hydrogens other than those in the alpha and beta positions with respect to silicon are replaced with fluorine.

Other possible substitutions include halogens, resulting in organic radicals such as chloropropyl, chloromethylpropyl, chloroisobutyl, bromoundecyl, chloroundecyl, perfluoroalkyl, and perfluoroalkylethyl. In addition, the hydrocarbons may contain other functionalities commonly associated with silane coupling agents including, but not limited to, amino, cyano, mercapto, sulfide, isothiocyanate, and isocyanate. Preferred organic radicals include n-octadecyl, n-octyl, 2-phenylethyl, 3-phenylpropyl, 4-phenylbutyl, 6-phenylhexyl, 3-chloropropyl, 3-chloro-2-methylpropyl, 3-aminopropyl, 3-amino-2-methylpropyl, 2-aminoethyl-3-aminopropyl, 2-aminoethyl-3-amino-2-methylpropyl, 3-diethylenetriaminopropyl, 3-glycidoxypropyl, 3-methacryloxypropyl, 3-mercaptopropyl, 3-mercapto-2-methylpropyl, 3-(N-methylamino)propyl, methoxypolyethyleneoxypropyl, methoxytriethyleneoxypropyl, tridecafluorooctyl, heptadecafluorodecyl, and nonafluorohexyl. Silyl esters (I), in which X is an alkoxy group, may be formed directly by hydrosilylation of the unsaturated species or by reaction of the aforementioned haloalkylsilanes, where X=chloro, fluoro, bromo, or iodo, under, for example, phase transfer-catalyzed or other substitution conditions.

Films, adhesives, and composites formed from the inventive dipodal silanes generally demonstrate significantly greater hydrolytic resistance and film-forming ability than both conventional silanes containing one silicon atom and bridged dipodal silanes containing two silicon atoms. These benefits arise from the presence of the two silicon atoms in close proximity to one another in the disilapropyl terminus. While not wishing to be bound by theory, it is believed that the increased hydrolytic stability is due to the additional oxane bonds formed with a substrate. Silicon-oxygen-silicon bonds in aqueous media are believed to have dissociation constants in the range of $1 \times 10^{-2}$ to $10^{-5}$. In order for a bond between a conventional monopodal silane and a substrate to fail, three oxane bonds must be dissociated, leading to a dissociation constant in the range of $10^{-6}$ to $10^{-9}$ in order for the silane to diffuse from the surface. The presence of the two additional bonds in the dipodal silanes decreases the probability of dissociation by a factor of at least 10,000.

Overly simplified for didactic purposes, if hydrolytic failure for a conventional silane occurs within one day, the additional bonding in the dipodal silane could extend the failure time to about 10,000 days. Again, not wishing to be bound by theory, the proximity of the bonding sites is also important for maintaining hydrolytic stability. If the bonding sites are far apart, one end of the silane may have all three bonds rupture and diffuse from the interface. However, if the bonding sites are in close proximity to each other, bond re-association is facilitated.

The pendant dipodal silanes according to the invention may be synthesized from hydridocarbosilanes, such as the preferred starting material 1,1,1,3,3-pentachloro-1,3-disilapropane (also called (dichlorosilylmethyl)trichlorosilane), as shown in Formula (II).

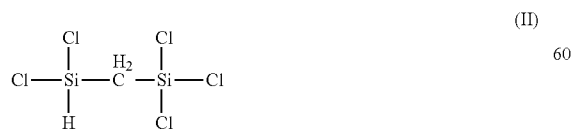

(II)

The 1,1,1,3,3-pentachloro-1,3-disilapropane may be reacted directly with an olefin by a hydrosilylation reaction or may be esterified to the corresponding pentaalkoxysilane derivative and then reacted with an olefin by a hydrosilylation reaction to yield the final desired product. As a simple example, octadecene may be reacted with 1,1,1,3,3-pentachloro-1,3-disilapropane (II) to form 1,1,1,3,3-pentachloro-1,3-disilaheneicosane. This compound may then be esterified with an alcohol to form, for example, 1,1,1,3,3-pentamethoxy-1,3-disilaheneicosane (from esterification with methanol) or reduced to form 1,3-disilaheneicosane. In some cases it is advantageous to form the esterified product, for example, 1,1,1,3,3-pentaethoxy-1,3-disilapropane, first, followed by hydrosilylation as the second step. This is especially important if the olefin reacts with chlorosilanes but does not react with alkoxy silanes. For example, the epoxy group of allylglycidyl ether reacts with chlorosilanes but is unreactive with alkoxy silanes.

The hydridocarbosilane starting material may also be substituted with halogens other than chlorine, such as bromine or fluorine, or with other hydrolyzable groups, such as dimethylamino, or acetoxy groups. It is not necessary for the hydridocarbosilane to be in pure form in order to accomplish the desired reaction. Rather, the hydridocarbosilane may be a component in a mixture containing related non-hydridosilanes such as, for example, a mixture of 1,1,1,3,3-pentachloro-1,3-disilapropane with bis(trichlorosilyl)methane. In fact, it may be desirable to use such a mixture for economic reasons because separation and purification of the hydrosilylation products from the chloro- or alkoxysilane may be more facile than the separation of the hydridosilane from the chloro- or alkoxysilane.

This invention will be further illustrated below in the following, non-limiting examples.

Example 1

Synthesis of
1,1,1,3,3-Pentachloro-1,3-disilatridecane

Under a nitrogen atmosphere a 1-liter, 3-necked flask equipped with a heating mantle, magnetic stirrer, pot thermometer, addition funnel and condenser was charged with 276.8 g of a mixture of approximately 46% (dichlorosilylmethyl)trichlorosilane and 54% bis(trichlorosilyl)methane [molar ratio 1:1]. The mixture was heated to 90° C. and 10 g of decene were added to the mixture via addition funnel, followed by 0.5 ml of 5% hexachloroplatinic acid in tetrahydrofuran. An immediate exotherm was observed and the reaction mixture changed from clear to dark brown. An additional 173 g of decene were added at an appropriate rate to maintain the temperature between 90 and 110° C. Upon completion of the addition, an additional 0.25 ml of 5% hexachloroplatinic acid solution was added and the mixture was stirred at 100° C. for 45 minutes. GC analysis of the mixture indicated the presence of some unreacted pentachlorodisilapropane. An additional 10 g of decene were added and the reaction mixture was stirred an additional 45 minutes at 100° C. Distillation provided 242 g (59%) of the title compound, bp 126° C./0.1 mm Hg, density @ 20° C. 1.180.

Example 2

Synthesis and Analysis of
1,1,1,3,3-Pentamethoxy-1,3-disilatridecane

The product of Example 1 was reacted with an excess of trimethylorthoformate at 80-120° C. The reaction was considered complete when 5 drops of the reaction mixture shaken with 1 ml of deionized water was neutral (pH: 6-7). Purification of reaction crude by distillation yielded the title compound in 82%, bp 123-4° C./0.1 mmHg, density @ 20° C. 0.9554, refractive index @ 20° C.: 1.4327. The title compound was evaluated for surface treatment stability by coating it onto a borosilicate glass slide. Other silanes (n-decyltriethoxysilane, 1,2-bis(trimethoxysilyl)decane, and 1,10-bis(trimethoxysilyl)decane) were also applied to similar slides for comparison and an HCl accelerated aging study for durability was performed. FIG. 1 shows a graph of sessile water contact angle in 6 M HCl versus static immersion time (days), a measure of stability. It can be seen that the contact angle of the 1,1,1,3,3-pentamethoxy-1,3-disilatridecane treated surface was maintained whereas the contact angle of the surfaces treated with other silanes was lower with time, indicating degradation of the bond to the borosilicate glass substrate.

Example 3

Synthesis of 2-[Methoxy(triethyleneoxy)]-1,1,1,3,3-pentachloro-1,3-disilahexane

Under an atmosphere of dry nitrogen, a 500-ml, 3-necked flask equipped with a heating mantle, magnetic stirrer, pot thermometer, addition funnel and condenser was charged with 51.1 g of allyloxy(triethyleneoxy)methyl ether. A 141.8 g mixture containing approximately 46% (dichlorosilylmethyl)trichlorosilane and 54% bis(trichlorosilyl)methane [molar ratio 1:1] was charged to the addition funnel. The reaction mixture was heated to 85° C. and 25 g of the chlorosilane mixture was added, followed by 0.25 ml of 5% hexachloroplatinic acid in tetrahydrofuran. An immediate exotherm was observed and the solution changed from clear to dark brown. The balance of the chlorosilane mixture was added at an appropriate rate to maintain a reaction temperature between 85 and 105° C. Upon completion of the addition of the silane mixture, an additional 0.25 ml of 5% hexachloroplatinic acid solution was added and the reaction mixture was stirred and heated at 95° C. for an additional 45 minutes. Purification by distillation yielded 80 g (70%) of the title compound, bp 170-2° C./0.4 mmHg, density @ 20° C. 1.262.

Example 4

Synthesis of [2-Methoxy(triethyleneoxy)propyl]-1,1,1,3,3-pentaethoxy-1,3-disilahexane The product of Example 3 was reacted with an excess of triethylorthoformate at 80-120° C. The reaction was considered complete when 5 drops of the reaction mixture shaken with 1 ml of deionized water was neutral (pH: 6-7). The reaction mixture was stripped at 120° C. under 1 mm Hg vacuum to yield the crude product which was further purified with WIFE to isolate the pure title compound: yield 56%, bp 170-2° C./0.1 mmHg, density @ 20° C. 0.994, refractive index @20° C.: 1.4359.

Example 5

Synthesis of 1,1,1,3,3-Pentaethoxy-1,3-disilahexylglycidylether

A 3-L flask equipped with magnetic stirring, pot thermometer, addition funnel and a dry ice condenser was charged with a 1200 g mixture containing approximately 29% of (diethoxysilylmethyl)triethoxysilane and 71% of bis(triethoxysilyl)methane [molar ratio 1:2.2], in addition to 0.1 g of phenothiazine. The addition funnel was charged with allyl glycidyl ether (114.1 g; 1 mol). The reaction mixture was heated to about 80° C. and 25 mL of the allyl glycidyl ether were added to initiate the reaction, after which the remainder of the olefin was added at an appropriate rate to maintain a temperature of 85 to 115° C. After the addition was complete, the reaction mixture was heated at 90° C. for an additional 45 minutes. Distillation of the product directly from the reaction mixture yielded 61 g (15%) of the title compound as a mixture of two isomers, bp 168-78° C./0.5 mm Hg, density @ 20° C. 1.003, refractive index @ 20°: 1.4330.

Example 6

Synthesis of 1,1,1,3,3,6-Hexachloro-5-methyl-1,3-disilahexane

A 2-L flask equipped with magnetic stirring, pot thermometer, addition funnel and condenser was charged with a mixture of 1455 g (2.05 mol) containing approximately 46% (dichlorosilylmethyl)trichlorosilane and 54% bis(trichlorosilyl)methane [molar ratio 1:1]. To the addition funnel were added 186 g (2.05 mol) of methallyl chloride. The reaction mixture was heated to 110° C. and 20 g of the olefin and 0.5 mL of a 5% solution of chloroplatinic acid in tetrahydrofuran were added to the reaction mixture to initiate the reaction. The remainder of the olefin was added to the reaction mixture at an appropriate rate to maintain the reaction temperature between 110 and 120° C. After completion of the olefin addition, the reaction mixture was heated to 130° C. for an additional 3 hours. Distillation of the product directly from the reaction mixture yielded 412 g (60%) of the title dipodal silane, bp 89-91° C./0.4 mm Hg, density @ 20° C. 1.380.

Example 7

Synthesis of 1,1,1,3,3-Pentaethoxy-6-chloro-5-methyl-1,3-disilahexane

The product of Example 6 was reacted with an excess of triethylorthoformate at 80-120° C. The reaction was considered complete when 5 drops of the reaction mixture shaken with 1 ml of deionized water was neutral (pH: 6-7). Distillation of the product directly from the reaction mixture yielded 60% of the title dipodal silane, bp 110° C./0.5 mm Hg, density @ 20° C. 1.020, refractive index @ 20° C.: 1.4290.

Example 8

Synthesis of 1,1,1,3,3-Pentaethoxy-6-[(2-aminoethyl)amino)]-5-methyl-1,3-disilahexane A 500-mL flask equipped with magnetic stirring, pot thermometer, addition funnel and condenser was charged with 96.8 g (0.30 mol) of 1,1,1,3,3-Pentaethoxy-6-chloro-5-methyl-1,3-disilahexane and 75.1 g of ethylenediamine. The reaction mixture was heated to 110° C. for 12 to 16 hours. 25 g of ethanol was then added into the pot. The reaction mixture was separated with a separatory funnel. Wiped-film purification of the bottom layer yielded 81 g (89%) of the title dipodal silane, bp (est) 130 to 150° C./0.5 mm Hg, density @ 20° C. 0.990, refractive index @20° C.: 1.4419.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A pendant dipodal silane having formula (I), wherein R is a linear or branched, saturated, substituted or unsubstituted hydrocarbon having about four to about thirty carbon atoms and X is selected from the group consisting of a halogen and an alkoxy group:

$$RSiX_2CH_2SiX_3 \quad (I);$$

and wherein the silane having formula (I) is selected from the group consisting of:
- a silane having formula (I), wherein X is chloro and R is 3-chloro-2-methylpropyl;
- a silane having formula (I), wherein X is methoxy and R is 3-chloro-2-methylpropyl;
- a silane having formula (I), wherein X is ethoxy and R is 3-chloro-2-methylpropyl;
- a silane having formula (I), wherein X is chloro and R is 3-cyanopropyl;
- a silane having formula (I), wherein X is ethoxy and R is 3-amino-2-methylpropyl;
- a silane having formula (I), wherein X is ethoxy and R is 2-aminoethyl-3-amino-2-methylpropyl;
- a silane having formula (I), wherein X is ethoxy and R is 3-glycidoxypropyl;
- a silane having formula (I), wherein X is methoxy and R is 3-methacryloxypropyl;
- a silane having formula (I), wherein X is ethoxy and R is 3-mercapto-2-methylpropyl;
- a silane having formula (I), wherein X is ethoxy and R is 3-(N-methylamino)propyl;
- a silane having formula (I), wherein X is ethoxy and R is methoxypolyethyleneoxypropyl;
- 1,1,1,3,3-pentachloro-1,3-disilatridecane; and
- 1,1,1,3,3-pentamethoxy-1,3-disilatridecane.

2. A pendant dipodal silane having formula (I), wherein R is a linear or branched, saturated or unsaturated substituted hydrocarbon having about four to about thirty carbon atoms, and wherein R is substituted with a functional group selected from the group consisting of an aromatic group, an ether group, an ester group, an epoxy group, a halogen, an amino group, a cyano group, a mercapto group, a sulfide group, an isothiocyanate group, and an isocyanate group; and X is selected from the group consisting of a halogen, an alkoxy group, a dialkylamino group, and an acetoxy group:

$$RSiX_2CH_2SiX_3 \quad (I).$$

3. A pendant dipodal silane having formula (I), wherein R is a linear or branched, saturated or unsaturated, substituted or unsubstituted hydrocarbon having about four to about thirty carbon atoms and X is selected from the group consisting of chloro, bromo, fluoro, a methoxy group, an ethoxy group, an acetoxy group, and a dialkylamino group:

$$RSiX_2CH_2SiX_3 \quad (I).$$

4. A pendant dipodal silane having formula (I), wherein R is a linear or branched substituted or unsubstituted alkyl group having about ten to about thirty carbon atoms and X is selected from the group consisting of a halogen, an alkoxy group, a dialkylamino group, and an acetoxy group:

$$RSiX_2CH_2SiX_3— \quad (I).$$

5. The silane according to claim 4, wherein the alkyl group has an aromatic terminus.

6. The silane according to claim 4, wherein the alkyl group has a halogen terminus selected from the group consisting of fluorine, chlorine, and bromine.

7. The silane according to claim 4, wherein all hydrogens other than hydrogens in alpha or beta positions with respect to silicon are replaced with fluorine.

8. A surface modified with a silane compound according to claim 1.

9. The surface according to claim 8, wherein the surface is glass.

10. A surface modified with a silane compound according to claim 2.

11. The surface according to claim 9, wherein the surface is glass.

12. A surface modified with a silane compound according to claim 3.

13. The surface according to claim 12, wherein the surface is glass.

14. A surface modified with a silane compound according to claim 4.

15. The surface according to claim 11, wherein the surface is glass.

* * * * *